United States Patent

Lawrence et al.

Patent Number: 5,116,968
Date of Patent: May 26, 1992

[54] MACROLIDE COMPOUNDS

[75] Inventors: Gordon C. Lawrence, Burnham; Michael J. Dawson, Ickenham; David Noble, Stock Mandeville; Michael V. J. Ramsay, South Harrow; Richard Bell, South Ruislip; Derek R. Sutherland, Chalfont St Giles; Edward P. Tiley, Pinner, all of England

[73] Assignee: American Cyanamid Company, Stamford, Conn.

[21] Appl. No.: 630,437

[22] Filed: Dec. 20, 1990

Related U.S. Application Data

[63] Continuation of Ser. No. 351,380, May 9, 1989, abandoned.

[30] Foreign Application Priority Data

May 10, 1988 [GB] United Kingdom ............... 8811036

[51] Int. Cl.⁵ .................. A61K 31/70; A61K 31/71; A61K 31/365; C07H 17/04
[52] U.S. Cl. ...................... 536/71; 435/76; 435/253.5; 548/407; 548/218; 549/264; 514/30; 514/292; 514/450; 71/88
[58] Field of Search ............... 549/264; 514/30, 292, 514/450; 536/7.1; 548/407, 218; 71/88

[56] References Cited

U.S. PATENT DOCUMENTS

| | | | |
|---|---|---|---|
| 4,696,945 | 9/1987 | Frei et al. | 514/450 |
| 4,857,509 | 8/1989 | Frei et al. | 514/450 |
| 4,900,753 | 2/1990 | Sutherland et al. | 514/450 |
| 4,910,219 | 3/1990 | Sutherland et al. | 514/450 |
| 4,912,090 | 3/1990 | Yanai et al. | 514/450 |
| 4,916,154 | 4/1990 | Asato et al. | 514/450 |
| 4,918,096 | 4/1990 | Ramsey et al. | 514/450 |
| 4,918,098 | 4/1990 | Ramsey et al. | 514/450 |

Primary Examiner—Ronald W. Griffin
Attorney, Agent, or Firm—Bacon & Thomas

[57] ABSTRACT

Compounds of formula (1)

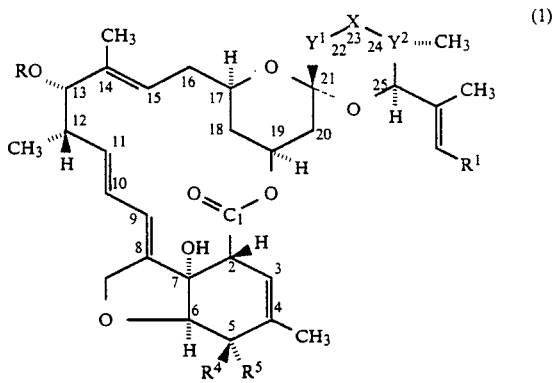

wherein
R represents a sugar residue or an acylated derivative thereof;
$R^1$ represents a methyl, ethyl or isopropyl group;
$Y^1$ is $-CH_2$, $Y^2$ is $-CH-$ and X represents

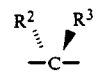

[wherein $R^2$ represents a hydrogen atom or a group $OR^6$ (where $OR^6$ is a hydroxyl group or a substituted hydroxyl group having up to 25 carbon atoms) and $R^3$ represents a hydrogen atom, or $R^2$ and $R^3$ together with the carbon atom to which they are attached represent $>C=O$, $>C=CH_2$ or $>C=NOR^7$ (where $R^7$ represents a hydrogen atom, a $C_{1-8}$ alkyl group or a $C_{3-8}$ alkenyl group) and the group $>C=NOR^7$ is in the E configuration] or $-Y^1-X-Y^2-$ represents $-CH=CH-CH-$ or $-CH_2-CH=C-$; and
$R^4$ represents a group $OR^6$ as defined above and $R^5$ represents a hydrogen atom, or $R^4$ and $R^5$ together with the carbon atom to which the are attached represent $>C=O$ or $>C=NOR^8$ (where $R^8$ is as defined above for $R^7$), and salts thereof. The compounds may be used to control nematode, acarine, insect or other pests.

9 Claims, No Drawings

MACROLIDE COMPOUNDS

This application is a continuation of application Ser. No. 07/351,380, filed May 9, 1989, now abandoned.

This invention relates to novel macrolide compounds having antibiotic activity, to processes for their preparation and to compositions containing them.

Thus, according to one aspect of the present invention we provide the compounds of formula (1)

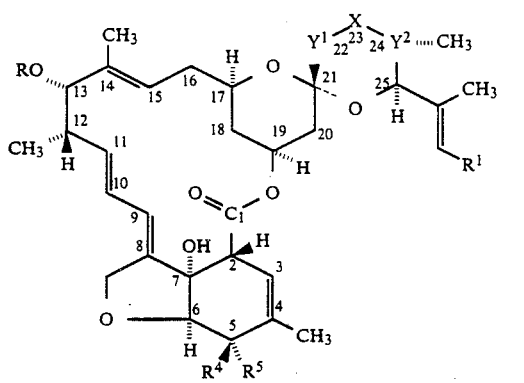

(1)

wherein
R represents a sugar residue or an acylated derivative thereof;
$R^1$ represents a methyl, ethyl or isopropyl group;
$Y'$ is —$CH_2$—, $Y^2$ is —CH— and X represents

[where $R^2$ represents a hydrogen atom or a group $OR^6$ (where $OR^6$ is a hydroxyl group or a substituted hydroxyl group having up to 25 carbon atoms) and $R^3$ represents a hydrogen atom, or $R^2$ and $R^3$ together with the carbon atom to which they are attached represent >C=O, >C=$CH_2$ or >C=$NOR^7$ (where $R^7$ represents a hydrogen atom, a $C_{1-8}$ alkyl group or a $C_{3-8}$ alkenyl group) and the group >C=$NOR^7$ is in the E configuration] or —$Y^1$—X—$Y^2$— represents —CH=CH—CH— or —$CH_2$—CH=C—; and
$R^4$ represents a group $OR^6$ as defined above and $R^5$ represents a hydrogen atom, or $R^4$ and $R^5$ together with the carbon atom to which the are attached represent >C=O or >C=$NOR^8$ (where $R^8$ is as defined above for $R^7$), and salts thereof.

The group $R^6$ when present in compounds of formula (I) may represent an acyl group e.g. a group of the formula $R^9CO$— or $R^9OCO$— or $R^9OCS$— (where $R^9$ is an aliphatic, araliphatic or aromatic group, for example an alkyl, alkenyl, alkynyl, cycloalkyl, aralkyl or aryl group), a formyl group, a group $R^{10}$ which is as defined above for $R^9$, a group $R^{11}SO_2$— (where $R^{11}$ is a $C_{1-4}$ alkyl or $C_{6-10}$ aryl group), a silyl group, a cyclic or acyclic acetal group, a group —$CO(CH_2)_nCO_2R^{12}$ (where $R^{12}$ is a hydrogen atom or a group as defined above for $R^9$ and n represents zero, 1 or 2) or a group $R^{13}R^{14}NCO$— (where $R^{13}$ and $R^{14}$ may each independently represent a hydrogen atom or a $C_{1-4}$ alkyl group).

Where $R^9$ or $R^{10}$ are alkyl groups, they may be for example $C_{1-8}$ alkyl groups, e.g. methyl, ethyl, n-propyl, i-propyl, n-butyl, i-butyl, t-butyl or n-heptyl which alkyl groups may also be substituted. Where $R^9$ is a substituted alkyl group it may be substituted by, for example, one or more, e.g. two or three, halogen atoms (e.g. chlorine or bromine atoms), or a carboxy, $C_{1-4}$ alkoxy (e.g. methoxy, ethoxy), phenoxy or silyloxy group. Where $R^{10}$ is a substituted alkyl group it may be substituted by a cycloalkyl e.g. cyclopropyl group.

Where $R^9$ and $R^{10}$ are alkenyl or alkynyl groups, they preferably have 2–8 carbon atoms and where $R^9$ and $R^{10}$ are cycloalkyl groups, they may be for example $C_{3-12}$ cycloalkyl, such as $C_{3-7}$ cycloalkyl, e.g. cyclopentyl groups.

Where $R^9$ and $R^{10}$ are aralkyl groups, they preferably have 1–6 carbon atoms in the alkyl moiety, and the aryl group(s) may be carbocyclic or heterocyclic and preferably contain 4–15 carbon atoms e.g. phenyl. Examples of such groups include phen $C_{1-6}$ alkyl e.g. benzyl groups.

Where $R^9$ and $R^{10}$ are aryl groups, they may be carbocyclic or heterocyclic and preferably have 4–15 carbon atoms e.g. phenyl.

When $R^6$ is a group $R^{11}SO_2$—, it may be for example a methylsulphonyl or p-toluenesulphonyl group.

Where $R^6$ represents a cyclic acetal group, it may for example have 5–7 ring members as in the tetrahydropyranyl group.

When $R^6$ represents a silyl group or $R^9$ contains a silyloxy substituent, the silyl group may carry three groups which may be the same or different, selected from alkyl, alkenyl, alkoxy, cycloalkyl, aralkyl, aryl and aryloxy groups. Such groups may be as defined above and particularly include methyl, t-butyl and phenyl groups. Particular examples of such silyl groups are trimethylsilyl and t-butyldimethylsilyl.

When $R^6$ represents a group —$CO(CH_2)_nCO_2R^{12}$, it may for example be a group —$COCO_2R^{12}$ or —$COCH_2CH_2CO_2R^{12}$ where $R^{12}$ represents a hydrogen atom or a $C_{1-4}$ alkyl group (e.g. methyl or ethyl).

When $R^6$ represents a group $R^{13}R^{14}NCO$—, $R^{13}$ and $R^{14}$ for example may each independently be a hydrogen atom or a methyl or ethyl group.

When $R^7$ or $R^8$ represents a $C_{1-8}$ alkyl group it may be for example a methyl, ethyl, n-propyl, i-propyl, n-butyl, i-butyl or t-butyl group, and is preferably a methyl group.

When $R^7$ or $R^8$ represents a $C_{3-8}$ alkenyl group it may be for example an allyl group.

When R is a sugar residue it may be, for example, a mono- or disaccharide. Examples of monosaccharides include pyranose and furanose sugars e.g. glucose, mannose, fructose, galactose, allose, gulose, talose, xylose, threose, lyxose, erythrose, altrose, ribose, arabinose, idose, 2-deoxyglucose, glucosamine, galactosamine, desosamine, mycaminose, angolosamine, forosamine, megosamine, chalcose, aldgarose, mycinose, mycosamine, mycarose, cladinose, oleandrose and 3-demethyloleandrose. Examples of disaccharides include α-L-oleandrosyl-α-L-oleandrose and α-3-demethyloleandrosyl-α-3'-demethyloleandrose.

Particular examples of the radical R include α-L-oleandrosyl-α-L-oleandrose, L-oleandrose, D-desosamine, D-mycaminose, D-angolosamine, D-forosamine, L-megosamine, D-chalcose, D-aldgarose, D-mycinose, D-mycosamine, L-mycarose and L-cladinose.

When R is an acylated sugar residue the sugar may be as described above and the acyl group may be as defined for the group $R^6$ above.

Compounds of formula (1) containing an acidic group may form salts with bases. Examples of such salts include alkali metal salts such as sodium and potassium salts.

Compounds of formula (1) in which R represents an α-L-oleandrose or α-L-oleandrosyl-α-L-oleandrose group are preferred.

In the compounds of formula (1) $R^1$ preferably represents an isopropyl group.

An important group of compounds of formula (1) is that in which $Y^1$ is —CH$_2$—, $Y^2$ is —CH— and X represents

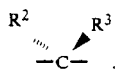

Particularly important compounds of this type are those in which $R^2$ is a hydrogen atom or a hydroxy, ethoxy or acetyloxy group and $R^3$ is a hydrogen atom or $R^2$ and $R^3$ together with the carbon atom to which they are attached represent >C=O, >C=CH$_2$ or >C=NOCH$_3$.

A further important group of compounds of formula (1) is that in which $R^4$ is a hydroxy, methoxy or acyloxy (e.g. acetyloxy) group or $R^4$ and $R^5$ together with the carbon atom to which they are attached represent >C=NOCH$_3$. $R^4$ preferably represents a hydroxyl group.

Important active compounds according to the invention are those of formula (1) in which:

R represents a α-L-oleandrosyl-α-L-oleandrose group, $R^1$ is an isopropyl group, $Y^1$ is —CH$_2$—, $Y^2$ is —CH—, X represents >C=NOCH$_3$, $R^4$ is a hydroxy group and $R^5$ is a hydrogen atom; and R represents a α-L-oleandrosyl-α-L-oleandrose group, $R^1$ is an isopropyl group, $Y^1$ is —CH$_2$—, $Y^2$ is —CH—, X represents —CH$_2$—, $R^4$ is a hydroxy group and $R^5$ is a hydrogen atom.

As indicated previously, compounds of the invention have antibiotic activity e.g. antihelminthic activity, for example against nematodes, and in particular, anti-endoparasitic and anti-ectoparasitic activity. Compounds of the invention may also be of use as intermediates in the preparation of other active compounds.

The antibiotic activity of the compounds of formula (I) may, for example, be demonstrated by their activity in vitro against free living nematodes e.g. *Caenorhabditis elegans.*

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

Furthermore, the compounds of formula (I) are also of use in combating insect, acarine and nematode pests in agriculture, horticulture, forestry, public health and stored products. Pests of soil and plant crops, including cereals (e.g. wheat, barley, maize and rice) vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti.*

According to the invention we therefore provide the compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or other vegetation) or to the pests themselves or a locus thereof.

The compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds of formula (I) may be formulated for use in veterinary or human medicine according to the general methods described in UK Patent Specification 2166436.

The total daily dosages of the compounds of the invention employed in both veterinary and human medicine will suitably be in the range 1-2000 μg/kg bodyweight, preferably from 50-1000 μg/kg and these may be given in divided doses, e.g. 1-4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulation will include the compound in association with a suitable carrier or diluent. Such carriers and diluents are as described in UK Patent Specification 2166436.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The rate at which a compound is applied depends upon a number of factors including the type of pest involved and the degree of infestation. However, in general, an application rate of 10 g/ha to 10 kg/ha will be suitable; preferably from 10 g/ha to 1 kg/ha for control of mites and insects and form 50 g/ha to 10 kg/ha for control of nematodes.

For use in veterinary medicine or for horticultural and agricultural use it may be desirable to use whole fermentation broth, as a source of the active compound. It may also be suitable to use dried broth (containing mycelia) or to use mycelia separated from the broth and pasteurised or more preferably, dried e.g. by spray-, freeze-, or roller drying. If desired the broth or mycelia may be formulated into compositions including conventional inert carriers, excipients or diluents as described above.

The antibiotic compounds of the invention may be administered or used in combination with other active ingredients.

In particular, the antibiotic compound of the invention may be used together with other antibiotic compounds. This may occur, for example, where whole fermentation broth is used without prior separation of compounds of the invention or where crude fermentation products are reacted according to the fermentation process of the invention without prior or subsequent separation; this may be preferable for example in agricultural use of a compound, where it is important to maintain low production costs.

The compounds according to the invention may be prepared by a number of processes as described in the following where $R^1$, $R^4$, $R^5$, X, $Y^1$ and $Y^2$ are as defined for general formula (1) unless specified otherwise. In some of these processes it may be necessary to protect a hydroxyl group at the 5-, 13- and/or 23-position in the starting material prior to effecting the reaction described. In such cases it may then be necessary to deprotect the same hydroxyl group once the reaction has occurred to obtain the desired compound of the invention. Conventional methods of protection and deprotection may be used, for example, as described in 'Protective Groups in Organic Synthesis' by Theodora W. Greene (Wiley-Interscience, New York 1981) and 'Protective Groups in Organic Chemistry' by J. F. W. McOmie (Plenum Press, London 1973). Thus, for example, an acyl group such as an acetyl group may be removed by basic hydrolysis e.g. using sodium hydroxide or potassium hydroxide or ammonia in an aqueous alcohol such as methanol.

Thus, according to another aspect of the invention, we provide a process for preparing a compound of formula (1) which comprises incubating a compound of formula (2)

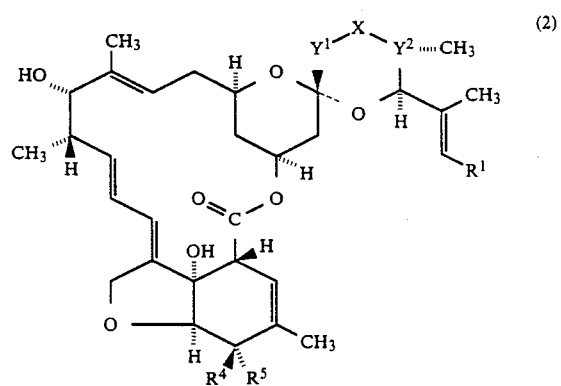

in a suitable medium in the presence of a microorganism or an enzyme derived therefrom or a preparation derived from a microorganism containing the enzyme of interest capable of effecting the conversion.

Suitable microorganisms and extracts thereof for use in the process according the invention may be identified by preliminary small scale tests designed to demonstrate ability of a microorganism or an extract thereof to convert compounds of formula (2) to compounds of formula (1). The formation of the compounds of formula (1) may be confirmed by suitable chromatographic analysis (e.g. high performance liquid chromatography) of the reaction mixture.

We have found microorganisms of the genus Streptomyces and extracts thereof to be particularly suitable for use in the process according to the present invention.

Particular Streptomyces microorganisms for use in the process according to the invention include strains of Streptomyces avermitilis, Streptomyces venezuelae, Streptomyces violaceoniger, Streptomyces erythaeus, Streptomyces spinichromogenes var. kujimyceticus, Streptomyces narbonensis, Streptomyces antibioticus, Streptomyces felleus, Streptomyces chryseus, Streptomyces flocculus, Streptomyces griseoflavus, Streptomyces lavendulae, Streptomyces eurythermus, Streptomyces hygroscopicus, Streptomyces halstedii, Streptomyces albogriseolus, Streptomyces cirratus, Streptomyces deltae, Streptomyces platensis, Streptomyces fungicidicus var. espinomyceticus, Streptomyces mycarofaciens, Streptomyces rimosus, Streptomyces djakartensis, Streptomyces platensis subsp malvinus, Streptomyces ambofaciens and Streptomyces fradiae and mutants of these strains.

Particularly suitable Streptomyces microorganisms for use in the process according to the invention include strains of *Streptomyces avermitilis* e.g. *Streptomyces avermitilis* ATCC 31272 and *Streptomyces avermitilis* ATCC 31780 and mutants thereof.

Mutants of the above strains may arise spontaneously or may be produced by a variety of methods including those described in UK Patent Specification 2166436.

Other microorganisms which may be used in the process according to the invention include fungi and plant cell preparations.

Examples of particular fungi for use in the process according to the invention include *Roccellaria mollis, Roccellaria galapagoensis, Schismatomma accedens, Ascochyta pisi, Cladosporium herbarum, Septoria nodorum* and *Stemphylium botryosum*.

Examples of plant cell preparations for use in the process according to the invention include *Phaseolus aureus, Petroselinum hortense, Glycine max, Phaseolus vulgaris, Nicotiana tabacum, Dioscorea deltoidea, Datura innoxia, Digitalis purpurea* and *Digitalis lanata*.

The bioconversion may also be effected using an organism containing the genetic material of one of the aforementioned microorganisms that participates in the synthesis of the compound of formula (1). Such organisms may be obtained using genetic engineering techniques including those outlined by D. A. Hopwood in 'Cloning genes for Antibiotic Biosynthesis in Streptomyces Spp.: Production of a hybrid antibiotic' p409–413 in Microbiology 1985, Ed. L. Lieve, American Society of Microbiology, Washington D.C. 1985. Such techniques may be used in a similar manner to that described previously for cloning antibiotic biosynthetic genes, including the biosynthetic genes for actinorhodin (Malpartida, F. and Hopwood, D. A. 1984, Nature 309, p462–464), erythromycin (Stanzak, R. et al, 1986, Biotechnology, 4, p229–232) and an important enzyme involved in penicillin and cephalosporin production in *Acremonium chrysogenum* (Sansom, S. M. et al, 1985, Nature, 318, p191–194).

Suitable enzymes for use in the process according to the present invention may be derived from an extremely wide range of sources. The aforementioned Streptomyces microorganisms, however, represent a particularly suitable source of enzymes capable of converting compounds of formula (2) into compounds of formula (1).

In one embodiment of the process according to the invention, the conversion of a compound of formula (2) into a compound of formula (1) may be effected by feeding the compound of formula (2) e.g. in a suitable solvent into a fermentation medium comprising the aforementioned microorganism in the presence of assimilable sources of carbon, nitrogen and mineral salts. Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt manganese, vanadium, chromium, calcium, copper, molybdenum, boron, phosphate, sulphate, chloride and carbonate ions.

An antifoam may be present to control excessive foaming and added at intervals as required.

The compound of formula (2) in a solvent such as a water miscible organic solvent (e.g. an alcohol such as methanol or propan-2-ol, a diol such as propan-1,2-ol or butan-1,3-ol, a ketone such as acetone, a nitrile such as acetonitrile, an ether such as tetrahydrofuran or dioxan, a substituted amide such as dimethylformamide or a dialkylsulphoxide such as dimethylsulphoxide) may be added at the beginning of the cultivation, or more usually, when the growth of the microorganism is under way, e.g. 2 to 4 days after the start of the cultivation.

Cultivation of the organism will generally be effected at a temperature of from 20° to 50° C., preferably from 25° to 40° C., and will desirably take place with aeration and agitation e.g. by shaking or stirring. The medium may initially be inoculated with a small quantity of a suspension of the sporulated microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 4.0 to 9.5, preferably 5.5 to 8.5 when a Streptomyces organism is present and preferably 4.0 to 8.5 when a fungus is present.

Once the compound of formula (2) has been added to the culture, usually with gentle mixing, the cultivation is continued such that the desired product is accumulated. The presence of the product in the fermentation broth may be determined by monitoring extracts of the broth by high performance liquid chromatography, and uv spectroscopy at 238 nm.

The product(s) may be isolated from the whole fermentation broth by conventional isolation and separation techniques as described in UK Patent Specifications 2166436 and 2176182.

When plant cells are used as part of the fermentation process it is preferable for the cultivation to be carried out using a plant medium containing a plant cell growth regulator such as indole acetic acid, naphthalene acetic acid, indole butyric acid, 2,4-dichlorophenoxyacetic acid, kinetin or benzylamino purine at a temperature of from 15° to 35° C. with the pH maintained within the range 5.0 to 7.5. Ammonium salts and nitrates also constitute the preferred sources of nitrogen present in the fermentation medium. Sucrose, fructose and glucose also constitute the preferred sources of carbon present in the fermentation medium.

In a further embodiment of the process according to the invention, the conversion of a compound of formula (2) into a compound of formula (1) may be effected by combining and incubating a compound of formula (2) e.g. in a suitable solvent (e.g. a water miscible organic solvent as previously defined) with a preparation of the enzyme of the invention and an appropriate sugar, desirably in a buffer solution, at, for example, 0° to 60°, preferably 20° to 40° e.g. about 28° C. The reaction will generally be carried out in the pH range 3.5 to 8.5 e.g.

5.5 to 7.5. When the reaction is complete, i.e. when the compound of formula (2) is no longer converted to the compound of the invention (as determined by monitoring extracts of the reaction mixture by high performance liquid chromatography and uv spectroscopy at 238 nm) the product is recovered by conventional isolation and separation techniques as described in UK Patent Specifications 2166436 and 2176182.

The enzyme for use in the process of the present invention may be prepared, for example, by culture of a microorganism which produces the enzyme in a nutrient medium. Suitable nutrient media and fermentation conditions for the preparation of the enzyme include those previously described for the preparation of a compound of formula (1) from a compound of formula (2) in the presence of a microorganism. The time at which the required enzymic activity reaches a maximum will, of course, vary according to the microorganism used and, hence, the optimum cultivation time is desirably determined independently for each strain employed.

For microorganisms where the enzyme is extracellular, the liquid culture medium or the filtrate after removal of whole cells may be used as a source of enzyme. Where the enzyme is cell-bound it may be released for use by conventional methods such as sonication, grinding with glass beads, homogenisation, treatment with lytic enzymes or with detergents, after suspension of the cells in a suitable buffer.

The resulting preparation, either with or without removal of cell debris, may be used as a source of enzyme. It is preferred, however, to purify the enzyme further by conventional means. Batch or column chromatography with ion-exchange celluloses or affinity adsorbents or other adsorbents e.g. hydroxylapatite may conveniently be employed. In addition, the enzyme may be concentrated or further purified by molecular sieve techniques e.g. ultrafiltration or salting out. In general, during purification procedures, it is desirable to maintain the pH within the range 3 to 11.

The enzyme may be employed in an immobilized form, e.g. by insolubilisation or entrappment thereof on or in a suitable matrix. Thus an extract of the enzyme may be bound or linked to an otherwise inert inorganic or organic polymer, entrapped on or in a fibre, or on or in a membrane or polymer such as polyacrylamide gel, adsorbed on an ion-exchange resin, crosslinked with a reagent such as glutaraldehyde, or occluded in an envelope such as a bead. Immobilized enzymes may advantageously be employed both in batch processes, after which the enzyme may be reused, and continuous flow processes wherein substrates pass through a column containing the immobilized enzyme.

In a particular embodiment of the fermentation process compounds of formula (1) in which $R^4$ is a hydroxy group are conveniently prepared from corresponding compounds of formula (2) in a suitable medium in the presence of a strain of *Streptomyces avermitilis* capable of effecting the conversion.

The fermentation process described above will generally produce the compounds of formula (1) in which R is a sugar residue. Acylated derivatives thereof may be prepared from the products of the fermentation process using standard N- and/or O-acylating conditions.

Intermediate compounds of formula (2) may be prepared by reducing a compound of formula (3)

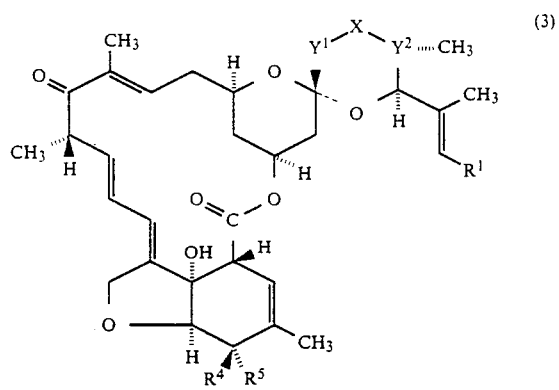

followed, if necessary, by removal of any protecting groups present.

The reduction may be effected for example using a reducing agent such as a borohydride, for example an alkali metal borohydride such as sodium borohydride or a lithium alkoxyaluminium hydride such as lithium tributoxyaluminium hydride.

The reaction involving a borohydride reducing agent takes place in the presence of a solvent such as an alkanol e.g. isopropyl alcohol or isobutyl alcohol conveniently at a temperature in the range of $-30°$ to $+80°$ C. e.g. at $0°$ C. The reaction involving a lithium alkoxyaluminium hydride takes place in the presence of a solvent such as an ether e.g. tetrahydrofuran or dioxan conveniently at a temperature in the range of $-78°$ to $0°$ C. e.g. at $-78°$ C.

Intermediate compounds of formula (3) may be prepared by oxidising a compound of formula (4)

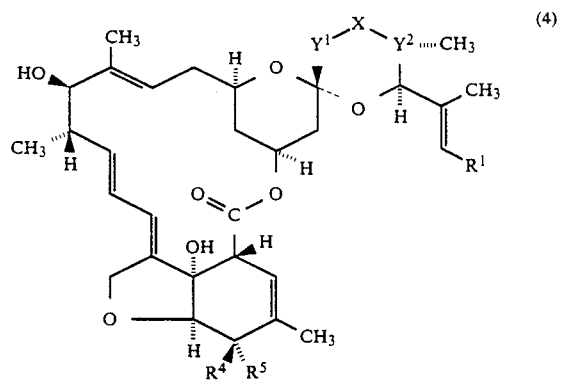

[wherein $R^4$ is as defined in formula (1) (except that it cannot represent a hydroxyl group)] followed, if necessary, by removal of any protecting groups present.

Suitable oxidising agents for the conversion include dialkylsulphoxides e.g. dimethylsulphoxide, in the presence of an activating agent such as N,N'-dicyclohexylcarbodiimide or an acyl halide, e.g. oxalyl chloride. The reaction may conveniently be effected in a suitable solvent such as a halogenated hydrocarbon e.g. methylene chloride at a temperature in the range of $-80°$ to $+50°$ C.

Intermediate compounds of formula (4) may be prepared by oxidising a compound of formula (5)

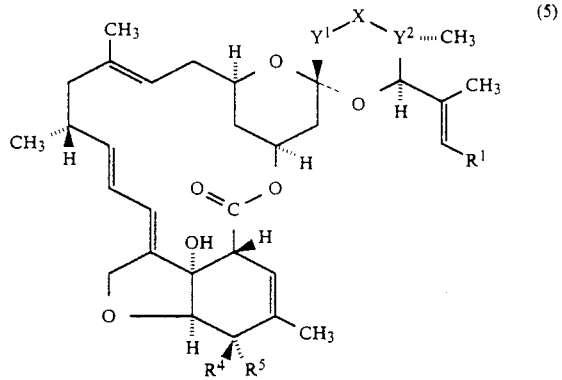

(5)

The oxidation may be effected for example with an oxidising agent such as selenium dioxide, preferably in the presence of an activator such as a peroxide, e.g. tert-butyl hydroperoxide. The reaction may conveniently be effected in an inert solvent such as a halogenated hydrocarbon e.g. dichloromethane, an ester, e.g. ethyl acetate or an ether, e.g. tetrahydrofuran, at a temperature in the range of 0° to 50° C., preferably at room temperature.

Alternatively, a compound of formula (5) may be treated with an oxidising agent described above in formic acid at a temperature of from 20° to 100° C. to provide a compound of formula (6)

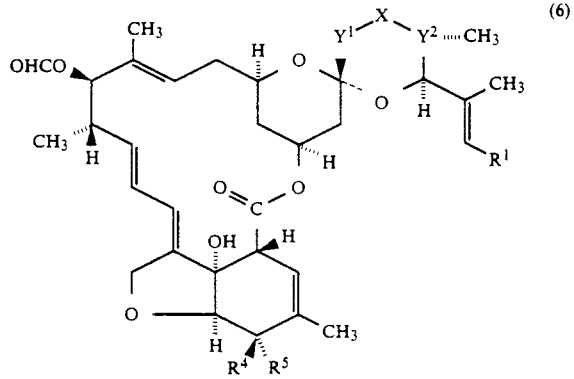

(6)

which, upon acid hydrolysis, e.g. using hydrochloric acid provides a compound of formula (4).

Intermediate compounds of formula (6) in which $Y^1$ is —$CH_2$—, $Y^2$ is —CH— and —X— represents >C=$NOR^7$ (wherein $R^7$ is as previously defined) may, if desired, be prepared from a corresponding compound of formula (6) in which $Y^1$ is —$CH_2$—, $Y^2$ is —CH— and —X— represents >C=O by reaction with a reagent $H_2NOR^7$.

The oximation reaction may conveniently be effected at a temperature in the range −20° to +100° C., e.g. −10° to +50° C. It is convenient to use the reagent $H_2NOR^7$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphosphoramide), ethers (e.g. cyclic cyclic ethers such as tetrahydrofuran or dioxan, and acylic ethers such as dimethoxyethane or diethylether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

Intermediate compounds of formula (5) in which $Y^1$ is —$CH_2$—, $Y^2$ is —CH—, and X represents

(where $R^2$ represents a hydrogen atom or a group $OR^6$ and $R^3$ represents a hydrogen atom or $R^2$ and $R^3$ together with the carbon atom to which they are attached represent >C=O), $R^4$ is a group $OR^6$ and $R^5$ is a hydrogen atom are known compounds described in UK Patent Specifications 2166436 and 2176182.

Intermediate compounds of formula (5) in which —$Y^1$—X—$Y^2$— represents —CH=CH—CH— or $CH_2$—CH=C—, $R^4$ is a group $OR^6$ and $R^5$ is a hydrogen atom are known compounds described in European Patent Specification 215654.

Intermediate compounds of formula (5) in which $Y^1$ is —$CH_2$—, $Y^2$ is —CH— and X represents >C=$CH_2$ may be prepared by reaction of a corresponding compound of formula (5) in which X is >C=O with an appropriate Wittig reagent e.g. a phosphorane of formula $(R^{13})_3P$=$CH_2$ (where $R^{13}$ is $C_{1-6}$ alkyl or aryl, e.g. monocyclic aryl such as phenyl). Suitable reaction solvents include ethers such as tetrahydrofuran or diethyl ether or a dipolar aprotic solvent such as dimethylsulphoxide. The reaction may be carried out at any suitable temperature e.g. at 0° C.

Intermediate compounds of formula (5) in which $Y^1$ is —$CH_2$—, $Y^2$ is —CH—, X represents >C=$NOR^7$ (where $R^7$ is as previously defined), $R^4$ is a group $OR^6$ and $R^5$ is a hydrogen atom or $R^4$ and $R^5$ together with the carbon atom to which they are attached represent >C=O, or intermediates in which X represents a group

(where $R^2$ is a hydrogen atom or a group $OR^6$ and $R^3$ is a hydrogen atom) or X represents >C=$NOR^7$ or —$Y^1$—X—$Y^2$— represents —CH=CH—CH— or —$CH_2$—CH=C— and $R^4$ and $R^5$ together with the carbon atom to which they are attached represent >C=$NOR^8$ may be prepared from the corresponding 5 and/or 23 keto compounds of formula (1) by reaction with a reagent $H_2NOR^7$ using the oximation reaction conditions previously described. It will be appreciated that in the preparation of a 5,23-bisoxime of formula (5) from a corresponding 5,23-diketone the groups >C=$NOR^7$ and >C=$NOR^8$ will be equivalent.

Intermediates of formula (5) in which $R^4$ and $R^5$ together with the carbon atom to which they are attached represent >C=O may be prepared by oxidation of the corresponding 5-hydroxy compounds in which $R^4$ is a hydroxy group.

The reaction may be effected with an oxidising agent serving to convert an allylic secondary hydroxyl group to an oxo group, whereby a compound of formula (5) is produced.

Suitable oxidising agents include, for example, transition metal oxides, such as manganese dioxide, and atmospheric oxygen in the presence of a suitable catalyst such as a finely divided metal e.g. platinum.

The oxidising agent will generally be used in excess over the stoichiometric quantity.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate. Combinations of such solvents either alone or with water may also be used.

The reaction may be carried out at a temperature of from $-50°$ C. to $+50°$ C., preferably from $0°$ to $30°$ C.

In a further process, the compounds of (1) in which $OR^6$ is a hydroxyl group may be prepared from a corresponding compound of formula (1) in which $OR^6$ is a substituted hydroxyl group. The conversion will usually be carried out in the context of removing a protecting group such as referred to above.

In a yet further process, the compounds of formula (1) in which $OR^6$ is a substituted hydroxyl group may generally be prepared by reacting the corresponding 5- and/or 23-hydroxy compound with reagent serving to form a substituted hydroxyl group.

The reaction will in general be an acylation, sulphonylation, etherification, silylation or acetalation, and the reaction may be carried out according to the general methods described in UK Patent specification 2176182.

Salts of acids of formula (1) may be prepared by conventional means, for example by treating the acid with a base or converting one salt into another by exchange of ion.

The invention is further illustrated by the following Preparations and Examples wherein the compound of formula (5) above in which $R^1$ is isopropyl, $Y^1$ is —CH$_2$—, $Y^2$ is —CH—, X represents

(where $R^2$ is a hydroxyl group and $R^3$ is a hydrogen atom), $R^4$ is a hydroxy group and $R^5$ is a hydrogen atom is referred to as 'Factor A'. Compounds according to the invention are named with respect to Factor A. All temperatures are in ° C.

INTERMEDIATE 1

(13R)-Hydroxy-23-desoxy Factor A, 5-acetate

23-Desoxy Factor A, 5-acetate (4.79 g, Example 112 in UK Patent Specification 2176182) was added to a stirred mixture of selenium dioxide (416 mg) and t-butyl hydroperoxide (3M in dichloromethane; 5 ml) in dichloromethane (30 ml). After stirring at room temperature for 30 h the reaction mixture was diluted with ethyl acetate (200 ml), washed with water and brine, and dried (Na$_2$SO$_4$). The solvent was evaporated and the residue purified by chromatography (250 g silica gel, Merck 9385). Elution with ethyl acetate: light petroleum (1:4→1:2) afforded the title compound (560 mg) as a pale yellow foam. $\nu_{max}$(CHBr$_3$) 3600, 3460 (OH), 1732 (OAc), 1712 (CO$_2$R), 993 cm$^{-1}$ (C-O); δ (CDCl$_3$) values include 0.69 (3H, t, J 5 Hz), 2.15 (3H,s), 3.32 (1H,m), 3.72 (1H, d, J 10 Hz), 4.05 (1H, d, J 5 Hz), 5.52 (2H,m).

INTERMEDIATE 2

13-Keto-23-desoxy Factor A, 5-acetate

A solution of dimethyl sulphoxide (92 μl) in dichloromethane (1 ml) was added dropwise over 2 min to a solution of oxalyl chloride (57 μl) in dichloromethane (2 ml) at $-50°$, under an atmosphere of nitrogen. After 5 min a solution of the compound of Intermediate 1 (213 mg) in dichloromethane (3 ml) was added dropwise over 2 min at $-50°$. After 30 min at $-50°$ to $-45°$, triethylamine (453 μl) was added. After 5 min the cooling bath was removed and the reaction mixture was allowed to warm to room temperature during 30 min. The reaction mixture was partitioned between dichloromethane (50 ml) and water (50 ml). The organic phase was separated and the aqueous phase extracted with dichloromethane (25 ml). The combined organic extracts were washed with 2M hydrochloric acid (75 ml), saturated sodium bicarbonate solution (75 ml) and brine (75 ml), and dried (Na$_2$SO$_4$). The solvent was evaporated and the residue purified by flash chromatography (35 g silica gel, Merck 9385). Elution with ethyl acetate: light petroleum (1:2) afforded the title compound (132 mg) as a white foam. $[\alpha]_D^{22} +256°$ (c0.6, CHCl$_3$); δ (CDCl$_3$) values include 1.76 (3H,s), 1.82 (3H,s), 2.16 (3H,s), 3.40 (2H,m), 5.09 (1H, d, J 9 Hz), 5.52 (2H,m), 6.26 (1H, t, J 8 Hz).

INTERMEDIATE 3

(13S)-Hydroxy-23-desoxy Factor A, 5-acetate

A solution of sodium borohydride (0.2M in ethanol; 3.63 ml) was added dropwise to a solution of Intermediate 2 (431 mg) in ethanol (15 ml) at $0°$. After 30 min at $0°$, the reaction mixture was diluted with ethyl acetate, washed with 2M hydrochloric acid, saturated sodium bicarbonate solution and brine, and dried (Na$_2$SO$_4$). The solvent was evaporated and the residue purified by flash chromatography (40 g silica gel, Merck 9385). Elution with ethyl acetate:light petroleum (1:3) afforded the title compound as a white foam (368 mg); δ (CDCl$_3$) values include 0.69 (3H,d,J5 Hz), 0.93 (3H,d,J6 Hz), 1.04 (3H,d,J6 Hz), 1.17 (3H,d,J6 Hz), 3.31 (1H,m), 4.00 (1H,s), 4.04 (1H,d,5 Hz), 5.52 (2H,m).

INTERMEDIATE 4

(13S)-Hydroxy-23-desoxy Factor A

Aqueous sodium hydroxide (1M; 87 μl) was added to a stirred solution of Intermediate 3 (38 mg) in methanol (1 ml) at $0°$. After 1.5 h at $0°$, the reaction mixture was diluted with ethyl acetate (25 ml), washed with water and brine, and dried (Na$_2$SO$_4$). The solvent was evaporated and the residue purified by flash chromatography (10 g silica gel, Merck 9385). Elution with ethyl acetate:light petroleum (1:2) gave the title compound as a white foam (31 mg); $\nu$max (CHBr$_3$) 3540, 3460 (OH), 1704 cm$^{-1}$ (CO$_2$R); δ (CDCl$_3$) values include 0.69 (3H,d,J5 Hz), 0.95 (3H,d,J6 Hz), 1.06 (3H,d,J6 Hz), 1.18 (3H,d,J6 Hz), 3.26 (1H,m), 3.96 (1H,d,J5 Hz), 4.01 (2H,s), 4.29 (1H,t,J5 Hz).

INTERMEDIATE 5

(13R)-Formyloxy-23-keto Factor A,5-acetate

To a slurry of selenium dioxide (120 mg) in formic acid (1 ml) stirring at 60° was added a solution of 23-keto Factor A, 5-acetate (420 mg, Example 18 in UK Patent Specification 2176182) in formic acid (3 ml). The reaction mixture was stirred at 60° for 6 mins, then poured into water (150 ml) and extracted with diethylether (4×50 ml). The organic phase was dried (MgSO4) and solvent removed to give a brown solid which was purified by medium pressure column chromatography on silica (100 g Merck kieselgel 60; 230–400 mesh). Elution with dichloromethane:ethyl acetate (16:1) gave the title compound as a cream foam (103 mg); $\nu$max (CHBr3) 3480 (OH) and 1714 cm$^{-1}$ (ester and ketone); $\delta$ (CDCl3) includes 0.86 (d,6 Hz,3H), 0.97 (d,6 Hz,3H), 1.02 (d,6 Hz,3H), 1.07 (d,6 Hz,3H), 1.76 (s,3H), 3.32 (m, 1H), 2.16 (s,3H), 4.06 (d,6 Hz,1H), 5.02 (d,10 Hz,1H), 5.53 (m,2H), 8.08 (s,1H).

INTERMEDIATE 6

(13R)-Formyloxy-23(E)-methoxyimino Factor A,5-acetate

To a solution of Intermediate 5 (80 mg) in methanol (8 ml) was added a solution of methoxyamine hydrochloride (29 mg) and sodium acetate (33 mg) in water (0.7 ml). The reaction mixture was stirred at room temperature for 3 h, then poured into ether (40 ml) and washed with water. The organic phase was dried (MgSO4) and solvent removed to give the title compound as a cream foam (79 mg); $\delta$ (CDCl3) includes 0.91 (d,6 Hz,3H), 0.97 (d,6 Hz,3H), 1.02 (d,6 Hz,3H), 1.07 (d,6 Hz,3H), 1.76 (s,3H), 2.16 (s,3H)m, 3.28 (d,15 Hz,1H), 1.91 (d,15 Hz,1H), 3.32 (m,1H), 3.83 (s,3H), 4.06 (d,6 Hz,1H), 5.04 (d,10 Hz,1H), 5.54 (m,2H), 8.09 (s,1H).

INTERMEDIATE 7

(13R)-Hydroxy-23(E)-methoxyimino Factor A,5-acetate

To a solution of Intermediate 6 (65 mg) in methanol (5 ml) was added 2N hydrochloric acid (0.1 ml). The reaction mixture was stirred at room temperature for 4 h, then poured into dichloromethane (60 ml) and washed with saturated sodium bicarbonate solution and water. The organic phase was dried (MgSO4) and solvent removed to give a foam which was purified by medium pressure column chromatography on silica (30 g, Merck Kieselgel 60, 230–400 mesh). Elution with dichloromethane:ethyl acetate (4:1) gave the title compound as a white foam (39 mg); $[\alpha]_D^{21}$ +126° (C=0.22, CH2Cl2). $\delta$ (CDCl3) includes 0.92 (d,6 Hz,3H), 0.96 (d,6 Hz,3H), 1.05 (d,6 Hz,3H), 1.12 (d,6 Hz,3H), 1.77 (s,3H), 2.17 (s,3H), 3.29 (d,15 Hz,1H), 1.91 (d,15 Hz,1H), 3.32 (m,1H), 3.70 (dd10,2 Hz,1H), 3.83 (s,3H), 4.04 (d,6 Hz,1H), 5.54 (m,2H).

INTERMEDIATE 8

13-Keto-23(E)-methoxyimino Factor A,5-acetate

To a solution of oxalyl chloride (0.24 ml) in freshly distilled dichloromethane (3.6 ml) stirring at −60° under nitrogen was added a solution of dimethyl sulphoxide (0.4 ml) in freshly distilled dichloromethane (3.6 ml). The solution was cooled to −65° and after 5 mins and a solution of Intermediate 7 (770 mg) in dichloromethane (6 ml) was added. The cooling bath was allowed to warm to −60° then the reaction mixture left a further 30 mins stirring at −60° to −50° C.

Triethylamine (1.5 ml) was added and the reaction mixture allowed to warm to room temperature. The reaction mixture was then poured into dichloromethane (100 ml) and the solvent removed under vacuum. Diethyl ether (60 ml) was added and the triethylamine salt filtered off. The ether was removed under vacuum to give a foam which was purified by medium pressure column chromatography on silica (180 g, Merck Kieselgel 60, 230–400 mesh). Elution with dichloromethane:ethyl acetate (14:1) gave the title compound as a beige foam (450 mg); $\delta$ (CDCl3) includes 0.92 (d,6 Hz,3H), 0.96 (d,6 Hz,3H), 1.01 (d,6 Hz,3H), 1.18 (d,6 Hz,3H), 1.76 (s,3H), 1.80 (s,3H), 2.16 (s,3H), 3.31 (d,15 Hz,1H), 1.93 (d,15 Hz,1H), 3.39 (m,1H), 3.84 (s,3H), 4.08 (d,6 Hz,1H), 5.54 (m,2H), 6.22 (t,9 Hz,1H).

INTERMEDIATE 9

(13S)-Hydroxy-23(E)-methoxyimino Factor A,5-acetate

To a solution of Intermediate 8 (620 mg) in ethanol (25 ml) stirring at 0° was added a solution of sodium borohydride (4.9 ml of a 0.2M solution in ethanol). The reaction mixture was stirred 0° for 30 mins, then poured into ethyl acetate (400 ml) and washed with 2N hydrochloric acid, saturated sodium bicarbonate solution, water and brine. The organic phase was dried (MgSO4) and solvent removed to give a beige foam which was purified by medium pressure column chromatography on silica (180 g, Merck Kieselgel 60, 230–400 mesh). Elution with dichloromethane:ethyl acetate (10:1) gave the title compound as a white foam (502 mg); $\delta$ (CDCl3) includes 0.92 (d,6 Hz,3H), 0.97 (d,6 Hz,3H), 1.05 (d,6 Hz,3H), 1.16 (d,6 Hz,3H), 1.76 (s,3H), 2.16 (s,3H), 3.29 (d,15 Hz,1H), 1.91 (d,15 Hz,1H), 3.32 (m,1H), 3.84 (s,3H), 4.00 (broad s,1H), 4.06 (d,6 Hz,1H), 5.53 (m,2H).

INTERMEDIATE 10

(13S)-Hydroxy-23(E)-methoxyimino Factor A

To a solution of Intermediate 9 (291 mg) in methanol (7 ml) stirring at 0° was added dropwise a solution of sodium hydroxide (17 mg) in water (0.6 ml). The reaction mixture was stirred at 0° for 2 h, then was poured into dichloromethane (75 ml) and washed with 2N hydrochloric acid (2×50 ml), water and brine. The organic phase was dried (MgSO4) and solvent removed to give a beige foam which was purified by medium pressure column chromatography on silica (80 g, Merck Kieselgel 60, 230–400 mesh). Elution with dichloromethane:ethyl acetate (4:1) gave the title compound as a white foam (228 mg). $\delta$ (CDCl3) includes 0.91 (d,6 Hz,3H), 0.96 (d,6 Hz,3H), 1.05 (d,6 Hz,3H), 1.17 (d,6 Hz,3H), 1.88 (s,3H), 3.29 (d,15 Hz,1H), 1.92 (d,15 Hz,1H), 3.27 (m,1H), 3.83 (s,3H), 3.96 (d,6 Hz,1H), 4.00 (broad s,1H), 4.28 (t,6 Hz,1H).

EXAMPLE 1

A slope of *Streptomyces avermitilis* ATCC 31272 was used to inoculate a 250 ml shake flask containing the medium A (25 ml):

|  | $gL^{-1}$ |
| --- | --- |
| D-Glucose | 2.5 |
| Malt Dextrose MD30E | 25.0 |
| Arkasoy 50 | 12.5 |

-continued

|  | $gL^{-1}$ |
|---|---|
| Molasses | 1.5 |
| $KH_2PO_4$ | 0.125 |
| Calcium carbonate | 1.25 |
| [3-(N-Morpholino)propanesulphonic acid] | 21.0 |
| Distilled water | as required |
| pH adjusted to 6.5 with $H_2SO_4$ before autoclaving. | |

The flask was incubated at 28° for 2 days on a rotary shaker (250 rpm) and a portion (5 ml) of this 2 day old culture was placed in a 50 ml shake flask and 50 μl of a 20 mg/ml solution of (13S)-hydroxy-23(E)-methoxyimino Factor A in methanol added. The flask was incubated at 28° for 5 days on a rotary shaker (250 rpm) after which time an equal volume of methanol was added. The shake flask and contents were shaken for 1 h, centrifuged to remove the cells and the supernatant evaporated in vacuo to 1 ml.

180 μl portions of the sample were fractioned on a column of Spherisorb S5 ODS-2 (100 mm×4.6 mm) with detection at 238 nm. A gradient solvent system was used at a constant flow of 3 ml/min between Solvent A (acetonitrile/water 1:1) and Solvent B (acetonitrile/water 65:35). The initial eluant contained 80% Solvent A and 20% Solvent B and after 10 min. 100% Solvent B. From each injection, uv absorbing peaks with retention ratios relative to unchanged substrate of 2.13 and 3.45 were collected and those peaks with identical retention ratios were combined and evaporated to yield (a) a compound of formula (1) in which R is α-L-oleandrosyl-α-L-oleandrosyl, $R^1$ is isopropyl, $Y^1$ is —$CH_2$—, $Y^2$ is —CH—, X is >C=$NOCH_3$, $R^4$ is a hydroxyl group and $R^5$ is a hydrogen atom (retention ratio 2.13); Mass spectra (Electron impact) m/z include 907, 795, 764, 620, 618, 566, 476, 408, 376 and 145 (negative CI, $NH_3$) m/z 943 ($M^-$), 925, 907 (positive CI, $NH_3$) m/z 961 $(M+NH_4)^+$, 944 $(MH)^+$ and (b) a compound of formula (1) in which R is α-L-oleandrosyl-α-L-oleandrosyl, $R^1$ is isopropyl, $Y^1$ is —$CH_2$—, $Y^2$ is —CH—, X is >C=$NOCH_3$, $R^4$ is a methoxy group and $R^5$ is a hydrogen atom (retention ratio 3.45); Mass spectra (Electron impact) m/z include 907, 827, 814, 795, 764, 670, 651, 376, 275, 264, 263, 257, 145, 127, 113, 95 and 87 (negative CI, $NH_3$) m/z 957 ($M^-$), 907 (M—H$_2$O—$CH_3$OH)— (positive CI, $NH_3$) m/z 975 $(M+NH_4)^+$, 958 $(MH)^+$.

EXAMPLE 2

2×25 ml volumes of medium A in 250 ml shake flasks were inoculated directly from a slope of *Streptomyces avermitilis* ATCC 31780 and cultured at 28° as a rotary shaker at a speed of 250 rpm, 2" throw for 2 days.

The contents of the flasks were used to inoculate 2.5 L of medium A in a 3.5 L fermenter containing polypropylene glycol 2000 (1.25 ml). The culture was maintained at 28° and agitated at 250 rpm and aerated at 1.25 L min$^{-1}$. After 2 days, 13(S)-hydroxy-23-desoxy Factor A (234 mg) in methanol (25 ml) was added followed by sinefungin (30 mg) in water (25 ml). At this stage the agitation and aeration rates were increased to 500 rpm and 2.5 L min$^{-1}$ respectively.

After 4 days the fermentation liquor was centrifuged, the supernatant decanted and the cells were washed with water (0.5 L) and centrifuged again. The water wash was added to the supernatant and this was extracted with ethyl acetate (4×0.25 L). The combined ethyl acetate extracts were evaporated in vacuo to give an oil. The cells were extracted with methanol and the combined methanol extracts were washed with hexane (4×0.1 L with 0.1 L water added at each stage) and the aqueous layer was then extracted with methylene chloride (3×0.2 L) and the combined methylene chloride layers were evaporated in vacuo to an oil. The oil from extraction of supernatant was extracted with acetonitrile (25 ml) and this solution was added to the oil derived from the cells and filtered. The filtrate was applied to a column (26×2 cm) of Sephadex LH20 in acetonitrile and fractions (10 ml) were collected after a foreun of (50 ml). Fractions 2-18 were combined, evaporated in vacuo to an oil which was dissolved in acetonitrile (15 ml) and water (1 ml) and submitted to preparative chromatography on Spherisorb S50DS-2 (25×2 cm) in a solvent of acetonitrile/water (7:3) at a flow rate of 25 ml/min and detention at λ238 nm. Fractions eluting between 43 to 46 min. from consecutive (1 ml) injections were combined, diluted with water (1:1) and pumped back onto the column and then eluted with acetonitrile. Evaporation of the acetonitrile in vacuo yielded an oil which was dissolved in methanol (2 ml) and passed down a column (100 ml) of Sephadex LH20 in methanol. Combination of fractions with $\lambda_{max}$ 244 nm and evaporation in vacuo again yielded an oil. This was once more dissolved in acetonitrile (4 ml) and fractionated (15 ml) on a column (25×2 cm) of Sephadex LH20 in acetonitrile. Combination of fractions 5-10, evaporation of these in vacuo, followed by lyophilisation of the residue from cyclohexane/acetone gave a compound of formula (1) in which R is α-L-oleandrosyl-α-L-oleandrosyl, $R^1$ is isopropyl, $Y^1$ is —$CH_2$—, $Y^2$ is —CH—, X is >$CH_2$, $R^4$ is a hydroxy group and $R^5$ is a hydrogen atom (19.3 mg) as a colourless solid, λ(MeOH) 231.2 inf. ($E_1^1$ 202), 240 inf. ($E_1^1$ 256), 244.6 ($E_1^1$ 278), 250 nm inf. ($E_1^1$ 206), νCHBr$_3$ 3570, 3550, 1705, 1040, 980 cm$^{-1}$.

A 125 MHz $^{13}$C nmr spectrum in CDCl$_3$ gave signals at about δ173.8, 139.5, 137.9, 137.8, 136.4, 134.6, 131.5, 124.5, 120.3, 118.4, 117.9, 98.4, 97.5, 94.5, 82.4, 81.5, 80.4, 80.2, 79.2, 79.0, 78.1, 76.0, 68.5, 68.3, 68.0, 67.6, 67.1, 56.3, 56.2, 45.6, 40.8, 39.6, 36.8, 35.5, 34.4, 34.1, 31.5, 27.5, 26.5, 22.8, 22.6, 20.1, 19.8, 18.2, 17.6, 17.5, 15.0 and 10.9.

500 MHz $^1$H N.m.r. spectrum gave signals at about δ3.78 (1H, dq, 10, 6), 3.82 (1H, dq, 10, 6), 3.18 (1H, t, 9), 3.22 (1H, t, 9) and 3.42 (6H, s).

MS (E.I.) 900 (M$^+$) 882, 756, 738, 612, 594, 576, 484, 333, 315, 261, 249, 221, 179, 145.

EXAMPLE 3

*Streptomyces avermitilis* ATCC 31272 was incubated with 13(S)-hydroxy-23-desoxy Factor A according to the method of Example 1.

180 μl portions of the sample obtained were fractionated on a column of Spherisorb S5 ODS-2 (100 mm×4.6 mm) with detection at 238 nm using acetonitrile/water (65:35) adjusted to pH 4.2 with acetic acid as eluant. The uv absorbing peak with a retention ratio relative to unchanged substrate of 1.87 was collected from each injection and those peaks with identical retention ratios were combined and evaporated in vacuo to yield a compound of formula (1) in which R is α-L-oleandrosyl, $R^1$ is isopropyl, $Y^1$ is —$CH_2$—, $Y^2$ is —CH—, X is >$CH_2$, $R^4$ is a hydroxy group and $R^5$ is a hydrogen atom (retention ratio 1.87); Mass spectra (Electron impact) m/z include 756 (M$^+$), 738, 720, 594, 576, 333, 315, 261, 249, 221, 179, 151 and 145 (negative CI, NH$_3$) m/z 756 (M$^-$).

The following are examples of formulations according to the invention. The term 'Active Ingredient' as used hereinafter means a compound of the invention.

MULTIDOSE PARENTERAL INJECTION

EXAMPLE 1

|  | % w/v | Range |
|---|---|---|
| Active ingredient | 2.0 | 0.1–6.0% w/v |
| Benzyl alcohol | 1.0 |  |
| Polysorbate 80 | 10.0 |  |
| Glycerol formal | 50.0 |  |
| Water for Injections | to 100.0 |  |

Dissolve the active ingredient in the polysorbate 80 and glycerol formal. Add the benzyl alcohol and make up to volume with Water for Injections. Sterilize the product by conventional methods, for example sterile filtration or by heating in an autoclave and package aseptically.

EXAMPLE 2

|  | % w/v | Range |
|---|---|---|
| Active ingredient | 4.0 | 0.1–7.5% w/v |
| Benzyl alcohol | 2.0 |  |
| Glyceryl triacetate | 30.0 |  |
| Propylene glycol | to 100.0 |  |

Dissolve the active ingredient in the benzyl alcohol and glyceryl triacetate. Add the propylene glycol and make up to volume. Sterilize the product by conventional pharmaceutical methods, for example sterile filtration, and package aseptically.

EXAMPLE 3

|  | % | Range |
|---|---|---|
| Active ingredient | 2.0 w/v | 0.1–7.5% w/v |
| Ethanol | 36.0 v/v |  |
| Non-ionic surfactant (e.g. Synperonic PE L44*) | 10.0 w/v |  |
| Propylene glycol | to 100.0 |  |

*Trademark of ICI

Dissolve the active ingredient in the ethanol and surfactant and make up to volume. Sterilize the product by conventional pharmaceutical methods, for example sterile filtration, and package aseptically.

EXAMPLE 4

|  | % | Range |
|---|---|---|
| Active ingredient | 2.0 w/v | 0.1–3.0% w/v |
| Non-ionic surfactant (e.g. Synperonic PE F68*) | 2.0 w/v |  |
| Benzyl alcohol | 1.0 w/v |  |
| Miglyol 840** | 16.0 v/v |  |
| Water for Injections | to 100.0 |  |

*Trademark of ICI
**Trademark of Dynamit Nobel

Dissolve the active ingredient in the Miglyol 840. Dissolve the non-ionic surfactant and benzyl alcohol in most of the water. Prepare the emulsion by adding the oily solution to the aqueous solution while homogenising using conventional means. Make up to volume. Aseptically prepare and package aseptically.

| Aerosol spray |  |  |
|---|---|---|
|  | % w/w | Range |
| Active Ingredient | 0.1 | 0.01–2.0% w/w |
| Trichloroethane | 29.9 |  |
| Trichlorofluoromethane | 35.0 |  |
| Dichlorodifluoromethane | 35.0 |  |

Mix the Active Ingredient with trichloroethane and fill into the aerosol container. Purge the headspace with the gaseous propellant and crimp the valve into position. Fill the required weight of liquid propellant under pressure through the valve. Fit with actuators and dustcaps.

TABLET

Method of Manufacture—Wet Granulation

|  | mg |
|---|---|
| Active Ingredient | 250.0 |
| Magnesium stearate | 4.5 |
| Maize starch | 22.5 |
| Sodium starch glycolate | 9.0 |
| Sodium lauryl sulphate | 4.5 |

Microcrystalline cellulose to tablet core weight of 450 mg Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

VETERINARY TABLET FOR SMALL/DOMESTIC ANIMAL USE

Method of Manufacture—Dry Granulation

|  | mg |
|---|---|
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

| Veterinary intrammary injection |  |  |  |
|---|---|---|---|
|  |  | mg/dose | Range |
| Active Ingredient |  | 150 mg | 0.05–1.0 g |
| Polysorbate 60 | 3.0% w/w | } to 3 g | } to 3 or 15 g |
| White Beeswax | 6.0% w/w |  |  |
| Arachis oil | 91.0% w/w |  |  |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

| Veterinary slow-release bolus | | |
|---|---|---|
| | % w/v | Range |
| Active Ingredient | | 0.25–2 g |
| Colloidal silicon dioxide | 2.0 | to required fill weight |
| Microcrystalline cellulose | to 100 | |

Blend the active ingredient with the colloidal silicon dioxide and microcrystalline cellulose by using a suitable aliquot blending technique to achieve a satisfactory distribution of active ingredient throughout the carrier. Incorporate into the slow release device and give (1) a constant release of active ingredient or (2) a pulsed release of active ingredient.

| Veterinary oral drench | | |
|---|---|---|
| | % w/v | Range |
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | | |
|---|---|---|
| | % w/w | Range |
| Active Ingredient | 4.0 | 1–20% w/w |
| Saccharin sodium | 2.5 | |
| Polysorbate 85 | 3.0 | |
| Aluminium distearate | 5.0 | |
| Fractionated coconut oil | to 100.0 | |

Disperse the aluminum distearate in the fractionated coconut oil and polysorbate 85 by heating. Cool to room temperature and disperse the saccharin sodium in the oily vehicle. Disperse the active ingredient in the base. Fill into plastic syringes.

| Granules for veterinary in-feed administration | | |
|---|---|---|
| | % w/w | Range |
| Active Ingredient | 2.5 | 0.05–5% w/w |
| Calcium sulphate, hemi-hydrate | to 100.0 | |

Blend the Active Ingredient with the calcium sulphate. Prepare the granules using a wet granulation process. Dry using a tray or fluid-bed drier. Fill into the appropriate container.

| Veterinary Pour-on | | |
|---|---|---|
| | % w/v | Range |
| Active Ingredient | 2.0 | 0.1 to 30% |
| Dimethyl sulphoxide | 10.0 | |
| Methyl Isobutyl ketone | 30.0 | |
| Propylene glycol (and pigment) | to 100.0 | |

Dissolve the active ingredient in the dimethyl sulphoxide and the methyl isobutyl ketone. Add the pigment and make up to volume with the propylene glycol. Fill into the pour-on container.

| Emulsifiable Concentrate | |
|---|---|
| Active ingredient | 50 g |
| Anionic emulsifier (e.g. Phenyl sulphonate CALX) | 40 g |
| Non-ionic emulsifier (e.g. Synperonic NP13)* | 60 g |
| Aromatic solvent (e.g. Solvesso 100) to 1 liter. | |

*Trademark of ICI

Mix all ingredients, stir until dissolved.

| Granules | | |
|---|---|---|
| (a) | Active ingredient | 50 g |
| | Wood resin | 40 g |
| | Gypsum granules (20–60 mesh) (e.g. Agsorb 100A) | to 1 kg |
| (b) | Active ingredient | 50 g |
| | Synperonic NP13* | 40 g |
| | Gypsum granules (20–60 mesh) | to 1 kg. |

*Trademark of ICI

Dissolve all ingredients in a volatile solvent e.g. methylene chloride, add to granules tumbling in mixer. Dry to remove solvent.

We claim:

1. Compounds of formula (1)

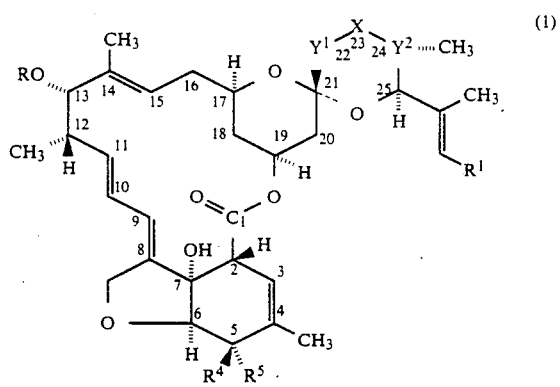

wherein
R represents a sugar residue or an acylated derivative thereof;
R¹ represents a methyl, ethyl or isopropyl group;
Y¹ is —CH₂, Y² is —CH— and X represents

[wherein R² represents a hydrogen atom or a group OR⁶ (where OR⁶ is a hydroxyl group or a substituted hydroxyl group having up to 25 carbon atoms) and $R^3$ represents a hydrogen atom, or $R^2$ and $R^3$ together with the carbon atom to which they are attached represent $>C=O$, $>C=CH_2$ or $>C=NOR^7$ (where $R^7$ represents a hydrogen atom, a $C_{1-8}$ alkyl group or a $C_{3-8}$ alkenyl group) and the group $>C=NOR^7$ is in the E configuration] or $-Y^1-X-Y^2-$ represents $-CH=CH-CH-$ or $-CH_2-CH=C-$; and $R^4$ represents a group $OR^6$ as defined above and $R^5$ represents a hydrogen atom, or $R^4$ and $R^5$ together with the carbon atom to which they are attached represent $>C=O$ or $>C=NOR^8$ (where $R^8$ is as defined above for $R^7$), and salts thereof.

2. Compounds according to claim 1 in which $R^1$ is an isopropyl group.

3. Compounds according to claim 1 in which R is an α-L-oleandrose or α-L-oleandrosyl-α-L-oleandrose group.

4. Compounds according to claim 1 in which $Y^1$ is $-CH_2-$, $Y^2$ is $-CH-$ and X represents $-C(R^2)(R^3)-$ where $R^2$ is a hydrogen atom or a hydroxy, ethoxy or acetyloxy group and $R^3$ is a hydrogen atom or $R^2$ and $R^3$ together with the carbon atom to which they are attached represent $>C=O$, $>C=CH_2$ or $>C=NOCH_3$; and $R^4$ is a hydroxy, methoxy or acetyloxy group or $R^4$ and $R^5$ together with the carbon atom to which they are attached represent $>C=NOCH_3$.

5. Compounds according to claim 1 in which: R represents α-L-oleandrosyl-α-L-oleandrose group, $R^1$ is an isopropyl group, $Y^1$ is $-CH_2-$, $Y^2$ is $-CH-$, X represents $>C=NOCH_3$, $R^4$ is a hydroxy group and $R^5$ is a hydrogen atom; and R represents a α-L-oleandrosyl-α-L-oleandrose group, $R^1$ is an isopropyl group, $Y^1$ is $-CH_2-$, $Y^2$ is $-CH-$, X represents $-CH_2-$, $R^4$ is a hydroxy group and $R^5$ is a hydrogen atom.

6. A pharmaceutical composition containing a pesticidally effective amount of at least one compound as claimed in claim 1 together with a pharmaceutically acceptable carrier.

7. A veterinary composition containing a pesticidally effective amount of at least one compound as claimed in claim 1 and a veterinary acceptable carrier.

8. A pesticidal composition containing a pesticidally effective amount of a compound as claimed in claim 1 and a pesticidally acceptable carrier.

9. A method of combatting insect, acarine or nematode pests which comprises applying an amount of a compound according to claim 1 effective in combatting pests to the pests or to a locus of the pests.

* * * * *